United States Patent [19]

Scheller

[11] Patent Number: 5,785,645
[45] Date of Patent: Jul. 28, 1998

[54] BEVELED TIP ILLUMINATOR FOR MICROSURGERY

[75] Inventor: Gregg D. Scheller, Chesterfield, Mo.

[73] Assignee: Synergetics, Inc., Chesterfield, Mo.

[21] Appl. No.: 633,031

[22] Filed: Apr. 16, 1996

[51] Int. Cl.$^6$ ........................................................ A61B 1/06
[52] U.S. Cl. ........................ 600/171; 600/160; 600/176; 600/177; 606/4; 606/107
[58] Field of Search ........................... 600/101, 160, 600/171, 176, 177, 182, 183, 249; 606/1, 2, 4, 5, 6, 15, 16, 107, 161

[56] References Cited

U.S. PATENT DOCUMENTS

| | | |
|---|---|---|
| 1,747,407 | 2/1930 | Wappler . |
| 2,235,979 | 3/1941 | Brown ........................................ 600/182 |
| 2,691,370 | 10/1954 | Wallace . |
| 3,835,841 | 9/1974 | Terada ................................... 600/171 X |
| 4,537,193 | 8/1985 | Tanner ............................................ 606/4 |
| 4,566,438 | 1/1986 | Liese et al. ........................... 600/171 X |
| 4,878,487 | 11/1989 | Sinnett . |
| 5,112,328 | 5/1992 | Taboada et al. ............................. 606/4 |
| 5,167,220 | 12/1992 | Brown ................................... 600/171 X |
| 5,213,569 | 5/1993 | Davis ..................................... 606/107 X |

FOREIGN PATENT DOCUMENTS 9301756  2/1993  WIPO ............................................ 606/6

Primary Examiner—Beverly M. Flanagan
Attorney, Agent, or Firm—Howell & Haferkamp, L.C.

[57] ABSTRACT

A manually manipulated illuminator used in microsurgery comprises an optic fiber that transmits light through the instrument and emits the light through a beveled end surface of the fiber, the beveled end surface having a leading edge that facilitates insertion of the end surface through an incision.

18 Claims, 1 Drawing Sheet

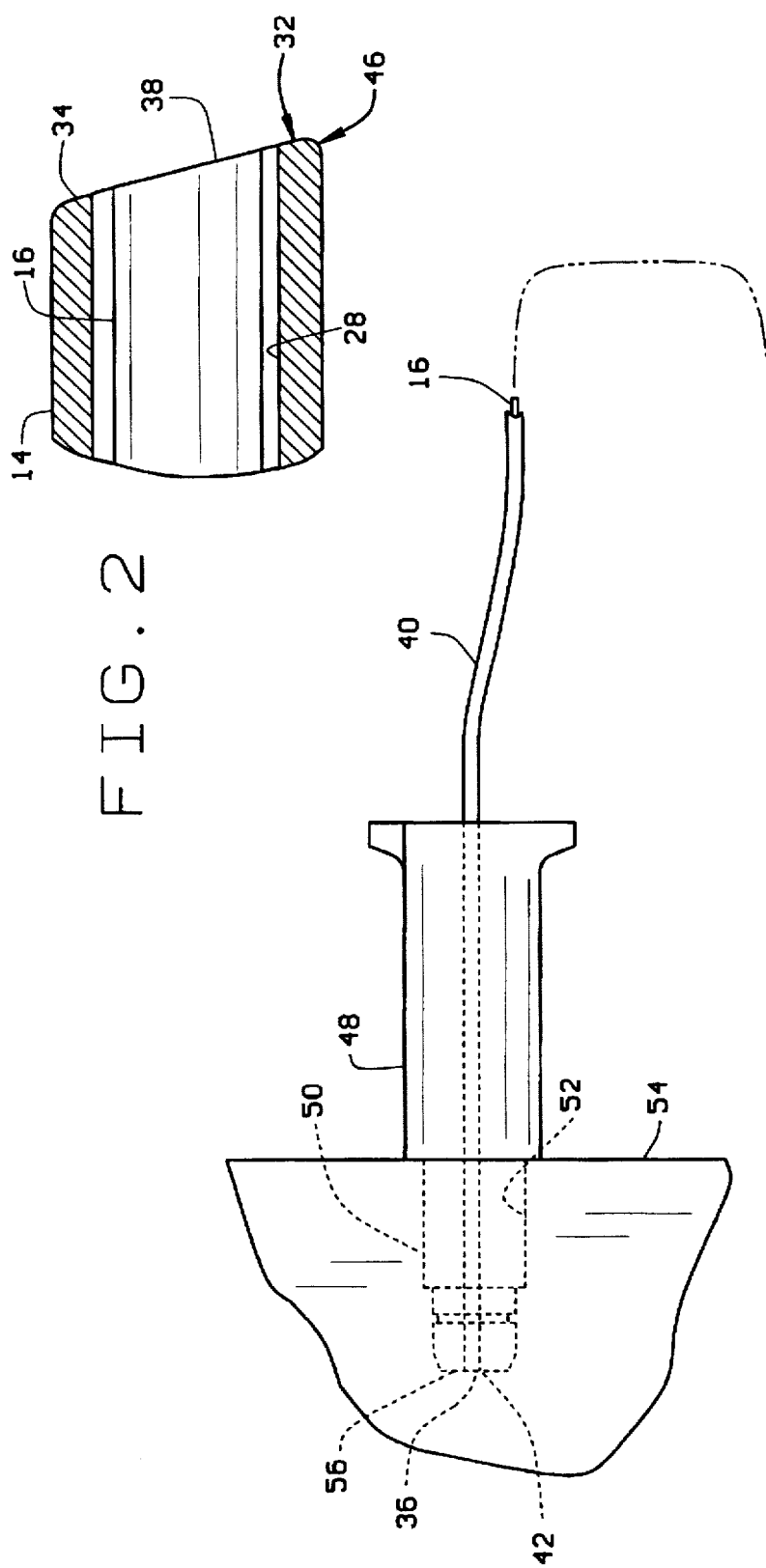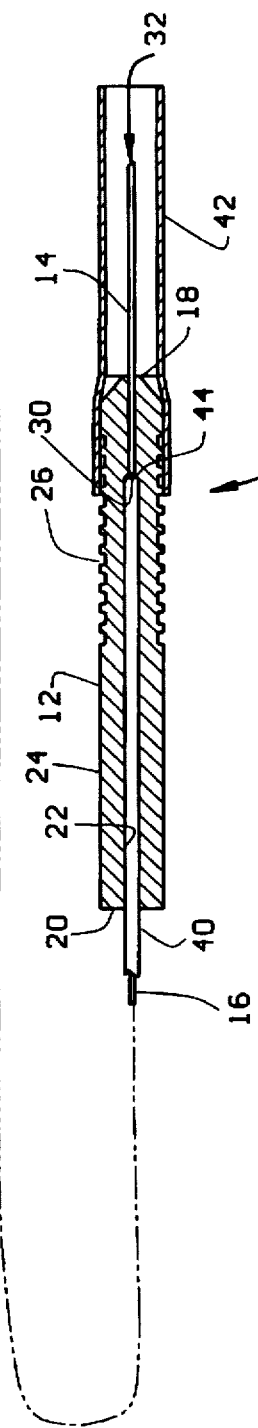

BEVELED TIP ILLUMINATOR FOR MICROSURGERY

BACKGROUND OF THE INVENTION (1) Field of the Invention

The present invention pertains to a manually manipulated illuminator used in microsurgery, and in particular ophthalmic surgery.

(2) Description of the Related Art

Although all types of surgery require a great deal of concentration and manual dexterity from the surgeon, perhaps one of the most intense types of surgery is ophthalmic surgery, or surgery of the eye. In ophthalmic surgery, the reduced size of the microsurgical instruments used and the minute area within the eye in which the surgery is performed demand a great deal from the surgeon's patience and skills. When considering that any unanticipated difficulties in using prior art microsurgical instruments in performing ophthalmic surgery could, in the least, add to the difficulty and mental strain of the surgeon in performing the surgery, or in the most, lead to complications in the functioning of the patient's eye, any modification to a microsurgical instrument making it easier for the surgeon to use is a significant contribution to the field of ophthalmic surgery.

In typical ophthalmic surgery, it is necessary that a light source be provided inside the patient's eye so that the rear wall of the eye, or other interior area of the eye where surgery is to be performed, is well illuminated enabling the surgeon to easily view the area of surgery. Most common ophthalmic surgery procedures involve first making a small incision into the eye interior for insertion of the illuminator, and making a second small incision into the eye interior for insertion of the instrument to be used by the surgeon in performing the particular surgery. With one hand, the surgeon must hold the light probe inserted through the first incision in the eye and with the other hand, the surgeon must hold the microsurgical instrument inserted through the second incision in the eye.

The typical microsurgical illuminator comprises a handle with a small cannula or cylindrical metal sleeve projecting from a distal end of the handle. An optic fiber having a proximal end connected to a source of light passes through the center of the handle and the cannula. The distal end of the optic fiber is positioned adjacent the distal end of the illuminator cannula. The distal end surface is planar and the plane of the distal end of the optic fiber is positioned normal to the center axis of the illuminator cannula and the center axis of the optic fiber passing through the cannula. As explained in the U.S. Pat. No. 4,878,487, it is preferable that the end surface of the fiber be ground to a smooth, flat surface that is perpendicular to the longitudinal axis 30 of the probe tip to limit the diffusion of light transmitted through the end surface and ensure the light beam is emitted generally straight ahead.

The incision made in the eye for insertion of the illuminator is very small, usually just large enough to permit the insertion of the illuminator cannula, typically a 20 gauge needle, through the incision. During surgery, there must be a close fit around the illuminator by the eye wall. The incision must seal around the instrument in order to maintain fluid pressure in the eye to keep the eye inflated. The fluid pressure is provided by saline solution supplied to the eye interior under a pressure head. With the incision being this small, the surgeon usually experiences a certain degree of difficulty in introducing the distal end surfaces of the illuminator cannula and optic fiber into the eye incision. This is primarily due to the incision being a slit incision and the distal end surface of the prior art illuminator being a flat, planar surface normal to the center axis of the illuminator cannula and optic fiber. This "difficulty" in introduction can cause severe inward deformation of the eye wall. This deformation may lead to the creation of a retinal detachment in this area.

SUMMARY OF THE INVENTION

It is an object of the present invention to eliminate the difficulties usually experienced by the surgeon in attempting to insert a microsurgical illuminator through an incision made in the eye by providing a modified construction of the illuminator distal end.

The microsurgical illuminator of the present invention is comprised of a handle, a cannula projecting from the distal end of the handle, and a length of optic fiber passing through the handle and the cannula. The proximal end of the optic fiber is provided with a connector for connecting the proximal end to any of the available sources of light typically used with microsurgical illuminators. The distal end of the optic fiber and the distal end of the illuminator cannula are both provided with flat, beveled surfaces. By beveled, what is meant is that the distal end surface of the optic fiber and the distal, annular end surface of the cannula are both formed at an oblique angle to the center axes of the cannula and the portion of the optic fiber passing through the cannula. In the preferred embodiment, the oblique angle formed by these end surfaces is 15° from a plane positioned normal or perpendicular to these axes. Forming these distal end surfaces with this oblique angle gives the illuminator distal end a leading edge that is much more easily inserted into an eye incision and significantly simplifies the task of inserting a microsurgical illuminator into an eye incision provided for the illuminator. The angled distal end surfaces also significantly reduce trauma to the tissues of the eye surrounding the incision.

BRIEF DESCRIPTION OF THE DRAWINGS

FIG. 1 is a fragmentary, side elevation view, partially in section, of the microsurgical illuminator of the present invention; and FIG. 2 is an enlarged side elevation view, partially in section, of the distal end of the microsurgical illuminator shown in FIG. 1.

DESCRIPTION OF THE PREFERRED EMBODIMENTS

The microsurgical illuminator 10 shown in FIG. 1 is described herein as used in ophthalmic surgery. However, it should be understood that this description is illustrative only and that the illuminator of the present invention may be used in other types of surgery and in other environments than that described.

With reference to FIG. 1, the microsurgical illuminator 10 of the present invention is basically comprised of a handle 12, a cannula or probe tip 14 projecting from the handle, and a length of optic fiber 16 passing the handle and cannula and having a length extending from the handle.

The handle 12 is elongated and has opposite distal 18 and proximal 20 ends. A center bore 22 having a center axis extends through the interior of the handle between its opposite ends. The exterior surface 24 of the handle has a circumferential dimension approximately that of a pen or pencil providing a familiar and comfortable feel to the surgeon's hand when holding the handle. A portion 26 of the handle exterior surface is ribbed or grooved, providing a gripping surface.

The cannula or probe tip 14 is a rigid, tubular sleeve preferably constructed of surgical steel. As shown in FIG. 2, the tip also has an interior bore 28 having a center axis that coaxial with the center axis of the handle. A end 30 of the tip is received in the interior bore of the handle at the handle distal end and is securely held therein. The tip projects axially from the handle distal end 18 for a significant portion of its length to a distal end 32 of the tip. The distal end of the tip can best be seen in FIG. 2, and is formed with a beveled, flat annular surface 34 surrounding the center bore 28 of the tip. In the preferred embodiment of the invention, the flat annular surface 34 at the tip distal end lies in a plane positioned at an angle of 15° to a plane normal or perpendicular to the center axis of the tip. However, in variations of the tip distal end surface 34, the annular surface may be positioned at an angle to the normal plane ranging between 30° and 5°.

The optic fiber 16 employed in the preferred embodiment of the illuminator is a single strand optic fiber. The fiber has a significant length, and has opposite proximal 36 and distal 38 end surfaces at the opposite ends of its length. A flexible, insulating tubing 40 surrounds the fiber and extends along the fiber from a proximal end 42 of the tubing at the fiber proximal end 36, to a distal end 44 of the tubing that ends at the proximal end 30 of the cannula tip 14. The optic fiber 16 extends axially beyond the tubing distal end 44 through the interior of the cannula tip 14 to the distal end 38 of the fiber positioned at the cannula tip distal end 32. As best seen in FIG. 2, the optic fiber distal end 38 has a flat, beveled planar surface. The angle of the optic fiber distal end surface 38 corresponds to the angle of the flat annular surface 34 of the tip distal end. In the preferred embodiment, the distal end surface 38 of the optic fiber is oriented at an angle of 15° to a planar surface that is positioned normal or perpendicular to the center axis of the optic fiber and the center axis of the cannula tip. In alternate embodiments of the invention, the angle formed between the optic fiber distal end surface 38 and the planar surface normal or perpendicular to the fiber and tip center axis may range between 30° and 5°.

Although an annular spacing is shown between the exterior of the optic fiber distal end 38 and the interior bore 28 of the tip, it should be understood that FIG. 2 is enlarged many times and that in the preferred embodiment, the optic fiber will fit snug in friction engagement in the interior bore of the tip. The angular orientation of the optic fiber distal end surface 38 and the tip annular end surface 34 gives the cannula tip a projecting leading edge 46 that can be used to locate an incision made for the tip in the eye and to then insert the tip through the incision. This leading edge as well as the entire outer annular edge of the cannula tip is rounded or radiused to further decrease trauma to the eye associated with insertion.

The proximal end 36 of the optic fiber is secured in the center of a light source connector 48. The connector has a plug end 50 that may have an exterior configuration complimentary to a connecting socket 52 of a commercially available light source 54. There are many different available light sources 54 used in microsurgery, and the connector plug 50 can be altered so that the illuminator 10 of the invention may be used with any of these available light sources. As is conventional in light source connectors for optic fiber illuminators, the proximal end of the optic fiber 36 extends completely through the connector 48 and its end surface 36 is positioned in the same plane as the proximal end surface 56 of the connector plug 50.

With the light source turned on and the connector plug 50 inserted into the socket 52, the light emitted within the light source is transmitted through the optic fiber 16 to its distal end 38. The light is then emitted from the distal end 38 of the optic fiber and may be used to illuminate an area of surgery. The tip leading edge 46 may be used to locate an incision made in the eye for the tip and to insert the tip through the incision. It can be appreciated that by needing only to insert the leading edge 46 into the incision, use of the illuminator of the invention in inserting the cannula tip distal end into the incision is much more easily performed than inserting the flat, planar end surface of the optic fiber and annular tip as done in the prior art. Moreover, because the angle of the optic fiber distal end surface in the preferred embodiment is only 15°, it does not appreciably diffuse the light emitted from the surface.

While the present invention has been described by reference to a specific embodiment, it should be understood that modifications and variations of the invention may be constructed without departing from the scope of the invention defined in the following claims.

What is claimed:

1. In a microsurgical illuminator dimensioned to be inserted through an incision in an eye to provide illumination to the eye interior, the illuminator comprising a handle having opposite proximal and distal ends and a bore with a center axis extending through the handle between its ends, an optic fiber passing through the handle bore, the optic fiber having a portion that projects from the handle distal end and terminates at an end surface, an improvement comprising the portion of the optic fiber having a center axis that is parallel to the bore center axis and that intersects the end surface obliquely.

2. The microsurgical illuminator of claim 1, wherein:
the end surface is a substantially planar surface.

3. The microsurgical illuminator of claim 1, wherein:
the handle bore has a center axis that is coaxial with the optic fiber portion center axis.

4. The microsurgical illuminator of claim 1, wherein:
a tubular sleeve projects from the handle distal end and the optic fiber portion extends through the tubular sleeve.

5. The microsurgical illuminator of claim 4, wherein:
the tubular sleeve has a distal end that is coplanar with the optic fiber end surface.

6. The microsurgical illuminator of claim 1, wherein:
the optic fiber end surface is oriented at an angle of 15° to a normal plane of the optic fiber center axis.

7. The microsurgical illuminator of claim 1, wherein:
the optic fiber end surface is oriented at an angle between 5° and 20° to a normal plane of the optic fiber center axis.

8. The microsurgical illuminator of claim 1, wherein:
the optic fiber end surface is oriented at an angle greater than 5° and less then 30° to a normal plane of the optic fiber center axis.

9. The microsurgical illuminator of claim 1, wherein:
the optic fiber has a proximal end opposite its end surface and a connector at its proximal end configured to connect to a light source.

10. In a microsurgical illuminator comprising
a handle having opposite proximal and distal ends and having a bore with a center axis extending through the handle between the handle ends and,
an improvement comprising passing through the handle bore and having a portion that projects from the handle distal end and terminates at a beveled end surface.

11. The microsurgical illuminator of claim 10, wherein:
a tubular sleeve projects from the distal end of the handle and the portion of the optic fiber passes through the sleeve, the sleeve has a distal end that is beveled.

12. The microsurgical illuminator of claim 11, wherein:
the beveled end surface of the optic fiber is planar and the beveled distal end of the sleeve is coplanar with the optic fiber end surface.

13. The microsurgical illuminator of claim 10, wherein:
the optic fiber has a center axis adjacent its beveled end surface and the beveled end surface is oriented at an angle greater than 5° and less than 30° to a plane normal to the optic fiber center axis.

14. The microsurgical illuminator of claim 10, wherein:
the optic fiber has a center axis adjacent its beveled end surface and the beveled end surface is oriented at an angle between 5° and 20° to a plane normal to the optic fiber center axis.

15. The microsurgical illuminator of claim 10, wherein:
the optic fiber has a center axis adjacent its beveled end surface and the beveled end surface is oriented at an angle of 15° to a plane normal to the optic fiber center axis.

16. The microsurgical illuminator of claim 10, wherein:
the optic fiber has a proximal end opposite its end surface and a connector at its proximal end configured to connect to a light source.

17. The microsurgical illuminator of claim 10, wherein:
the optic fiber has a center axis that is parallel to the handle bore center axis.

18. The microsurgical illuminator of claim 10, wherein:
the optic fiber has a center axis that is coaxial with the handle bore center axis.

* * * * *